US012782333B2

(12) United States Patent
Brevik et al.

(10) Patent No.: US 12,782,333 B2
(45) Date of Patent: Nov. 3, 2026

(54) APPARATUS AND METHOD FOR ANALYSING DRILLING FLUID

(71) Applicant: Equinor Energy AS, Stavanger (NO)

(72) Inventors: Jan Ove Brevik, Stavanger (NO); Åsmund Hjulstad, Stavanger (NO); Arne Voskamp, The Hague (NL); Robert Klein Breteler, Berkel en Rodenrijs (NL); Jelmer Braaksma, Delfgauw (NL)

(73) Assignee: EQUINOR ENERGY AS, Stavanger (NO)

(*) Notice: Subject to any disclaimer, the term of this patent is extended or adjusted under 35 U.S.C. 154(b) by 1099 days.

(21) Appl. No.: 17/760,928

(22) PCT Filed: Sep. 15, 2020

(86) PCT No.: PCT/NO2020/050238
§ 371 (c)(1),
(2) Date: Mar. 16, 2022

(87) PCT Pub. No.: WO2021/054840
PCT Pub. Date: Mar. 25, 2021

(65) Prior Publication Data

US 2022/0341313 A1 Oct. 27, 2022

(30) Foreign Application Priority Data

Sep. 17, 2019 (GB) ..................................... 1913400

(51) Int. Cl.
*G01N 33/28* (2006.01)
*G01J 3/28* (2006.01)
(Continued)

(52) U.S. Cl.
CPC ........ *G01N 33/2823* (2013.01); *G01J 3/2823* (2013.01); *G06T 7/246* (2017.01);
(Continued)

(58) Field of Classification Search
CPC ......... G01N 33/2823; G01N 2021/178; G01N 21/31; G01J 3/2823; G06T 7/246;
(Continued)

(56) References Cited

U.S. PATENT DOCUMENTS 7,639,741 B1 * 12/2009 Holt ....................... H04N 19/80 375/240.27
9,016,399 B2 4/2015 Pelletier et al.
(Continued)

FOREIGN PATENT DOCUMENTS

CN 108332853 A 7/2018
EP 2 689 278 A1 1/2014
(Continued)

OTHER PUBLICATIONS

Han et al., "Real-Time Borehole Condition Monitoring using Novel 3D Cuttings Sensing Technology" (SPE/IADC-184718-MS), SPE/IADC Drilling Conference and Exhibition, Mar. 14-16, 2017, total 18 pages.
(Continued)

*Primary Examiner* — Shelby A Turner
(74) *Attorney, Agent, or Firm* — Birch, Stewart, Kolasch & Birch, LLP

(57) ABSTRACT

A system and method of analysing drilling cuttings using image data output from a hyperspectral imaging device and at least one optical camera, includes generating a hyperspectral imaging data set including a plurality of lines of hyperspectral data derived from line images taken by the hyperspectral imaging device positioned along a drilling fluid cuttings path, obtaining tracking information in respect of particles of interest from the output of the at least one optical camera, correcting the position of pixels associated with particles of interest in the plurality of lines of hyperspectral imaging data based on the obtained tracking infor-
(Continued)

mation to generate corrected hyperspectral imaging data, and analysing the corrected hyperspectral imaging data to characterise the cuttings.

17 Claims, 4 Drawing Sheets

(51) Int. Cl.
*G06T 7/246* (2017.01)
*G06V 10/28* (2022.01)
*G06V 10/58* (2022.01)

(52) U.S. Cl.
CPC .............. *G06V 10/28* (2022.01); *G06V 10/58* (2022.01); *G06T 2207/10036* (2013.01); *G06V 2201/07* (2022.01)

(58) Field of Classification Search
CPC ......... G06T 2207/10036; G06T 7/0004; G06T 2207/10016; G06T 2207/10028; G06V 10/28; G06V 10/58; G06V 2201/07; E21B 47/002; E21B 49/005
See application file for complete search history.

(56) References Cited

U.S. PATENT DOCUMENTS

2009/0001269 A1 1/2009 Tadano
2012/0242822 A1* 9/2012 Rodney .................... G01V 8/10 348/81
2014/0177932 A1* 6/2014 Milne ................ G01N 21/8851 382/128
2016/0130928 A1* 5/2016 Torrione ............... E21B 49/005 700/275
2016/0266275 A1 9/2016 Akkurt et al.
2017/0089153 A1* 3/2017 Teodorescu ........... E21B 21/065
2021/0004933 A1* 1/2021 Wong .................... G06T 17/205

FOREIGN PATENT DOCUMENTS

EP 2 689 278 B1 11/2016
WO WO 2013/089683 A1 6/2013
WO WO 2015/002653 A1 1/2015
WO WO 2015/059058 A1 4/2015
WO WO 2016/077521 A1 5/2016
WO WO 2017/095557 A1 6/2017
WO WO-2019241114 A1 * 12/2019 ........... B07C 5/3422

OTHER PUBLICATIONS

International Search Report, issued in PCT/NO2020/050238, dated Nov. 25, 2020.
United Kingdom Examination Report and Notification of Intention to Grant under Section 18(4), issued in Priority Application No. 1913400.6, dated Dec. 14, 2021.
United Kingdom Search Report, issued in Priority Application No. 1913400.6, dated Feb. 25, 2020.
Written Opinion of the International Searching Authority, issued in PCT/NO2020/050238, dated Nov. 25, 2020.

* cited by examiner

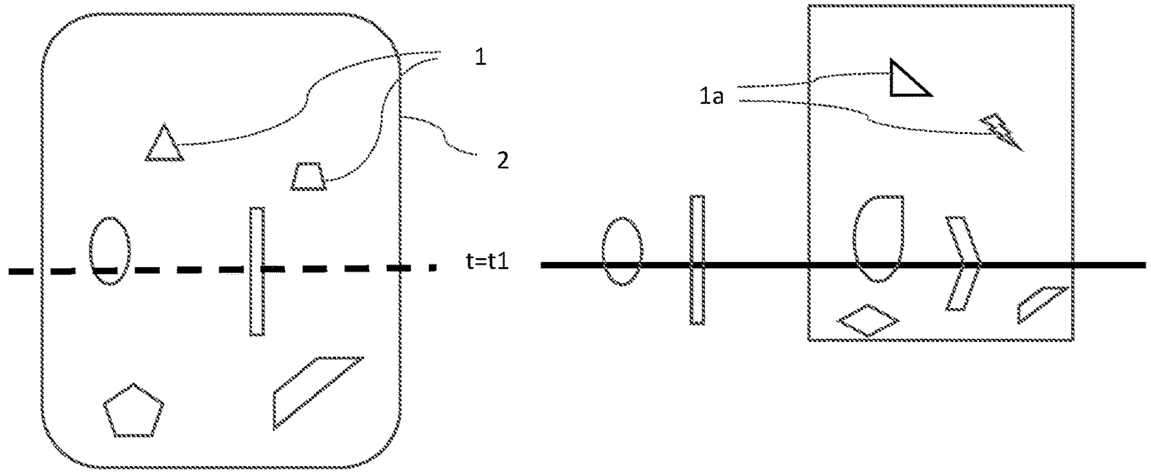
Fig. 2
Fig. 3
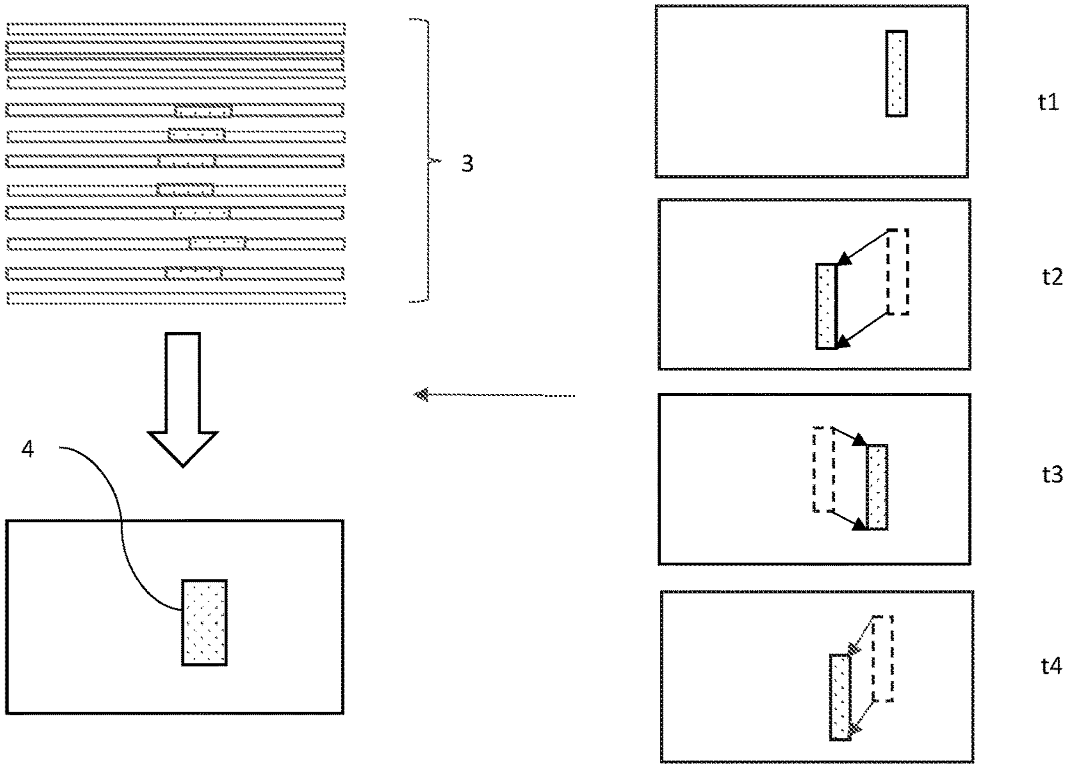

APPARATUS AND METHOD FOR ANALYSING DRILLING FLUID

FIELD

The invention relates to a method and system for analysing drilling fluid and, in particular, characterisation of the cuttings and cavings in drilling fluid.

BACKGROUND

EP-A-2689278 (U.S. Pat. No. 9,016,399) discloses the use of hyperspectral imaging on a shaker. Cuttings are retrieved from a well bore while drilling the formation and a hyperspectral image of the cuttings is continuously obtained and analysed to determine formation characteristics. The hyperspectral image capture mechanism is preferably placed on the disposal path after the shale shaker because the shale shaker is not stationary. Aligning successive frames is considered by cross correlating a set of hyperspectral components for stacking or averaging.

WO2013-A-089683 discloses the use of one of more visible light cameras, and/or infrared cameras. The camera or cameras may be located at a screen which may form part of a shaker table. There is no disclosure of any interaction between multiple image capture feeds. Drilling cuttings information and drilling mud information in the video stream can be removed according to this disclosure by reducing the number of wavelength of light. The data from the live video stream is then analysed to determine one or more of shape, size distribution, or volume of the downhole cuttings. Particle size analysis and shape recognition software is known according to this disclosure, e.g. face recognition software.

WO2016-A-077521 discloses systems and methods principally for detecting the fluid front on a shaker table for improving the operation of the shaker tables. The system may include multiple sensors and use of computer vision, in particular discloses determination of the height of the cuttings distinguished from background "height". The sensors include optical or video cameras, single or multi-stereo-cameras, night vision cameras, IR, LIDAR, RGB-D cameras, or other recording and/or distance-sensing equipment. Also disclosed is tracking of cuttings as they move across the shaker using video camera and motion estimation techniques. The information from the cameras is specifically disclosed as being combined with information from "other sensors", which are identified as related to the circulation system and providing information related to, flow-in, drilling pumps, flow-out, and/or pit volume. Cuttings are identified by, for example, background subtraction and/or change detection, because the cuttings appear different than the background, and appear to move at constant speed. Alternatively, image texture, reflectivity, and/or colour properties may be used to identify cuttings. Tracking may be performed by persistence or other motion tracking techniques (Kalman filters, particle filters) as cuttings will have substantially constant size and shape during travel. IR, hyperspectral imaging are mentioned but only in connection with their use in the techniques discussed in relation to optical cameras etc. WO2016-A-077521 describes annotating an image of the shaker tables, identifying key feature, such as the fluid front, cuttings, any potential issues, etc.

Han, Runqi, et al, discloses in "Real-Time Borehole Condition Monitoring using Novel 3D Cuttings Sensing Technology" (SPE/IADC-184718-ms), SPE/IADC Drilling conference 14-16 Mar. 2017, automation of cuttings monitoring to improve drilling efficiency and safety, by monitoring cuttings volume, size distribution, and cavings shape in real-time. The paper reviews the known techniques for Computer Vision, specifically for determining physical distance. The paper suggests that the best place for the monitoring systems is above the cuttings ramp where the cuttings slide down to the collecting pit—below the shaker table area is less affected by vibration, is protected from the environment, and the cuttings slide down the ramp at a relatively steady speed. A commercially available 2D laser profile scanner and 3D structured light cameras are proposed as a suitable depth sensing technology. A 2D HD camera was used to measure cuttings speed and to analyse size distribution of the cuttings. By synchronising the cuttings speed with the laser scanning frequency, a 3D profile of cuttings can be generated and the volume can be determined, according to this paper. Cuttings speed, and cuttings size distribution are calculated by computer vision algorithms. In addition the shape and size of the cuttings in 3D is determined from the 3D construction.

SUMMARY

The invention in one aspect combines hyperspectral imaging and one or more (high-speed) cameras for the purposes of describing the contents of drilling fluid returned from a downhole drilling process and characterising the cuttings and cavings (hereinafter referred to as cuttings for convenience). Conveniently the inspection is performed whilst the cuttings are traversing a shaker table, or other convenient surface in the drilling cuttings disposal path.

In an aspect the invention provides a method of analysing drilling cuttings using image data output from a hyperspectral imaging device and at least one optical camera, comprising, generating a hyperspectral imaging data set comprising a plurality of lines of hyperspectral data derived from line images taken by the hyperspectral imaging device positioned along a drilling fluid cuttings path, obtaining tracking information in respect of particles of interest from the output of the at least one optical camera, correcting the position of pixels associated with particles of interest in the plurality of lines of hyperspectral imaging data based on the obtained tracking information to generate corrected hyperspectral imaging data, and analysing the corrected hyperspectral imaging data to characterise the cuttings.

The method may further comprise, distinguishing between background and particles of interest in the optical camera output of a portion of the drilling fluid cuttings path that includes the hyperspectral imaging line position, and differentiating between particles of interest and background in the hyperspectral imaging data based on the step of distinguishing.

The method may further comprise tracking movement of particles in the optical camera output to obtain the tracking information and associating the particles of interest with the tracking information.

The method may further comprise obtaining depth information, wherein the particles of interest are distinguished from the background using the depth information.

Differentiating between particles of interest and background in the hyperspectral imaging data may comprise masking particles of interest in the optical data based on the step of distinguishing, and applying the mask to the hyperspectral imaging data to differentiate between particles of interest and background in the hyperspectral imaging data.

Associating the particles of interest with tracking information may comprise determining the speed of movement associated with pixels in the optical camera output.

The portion of the drilling fluid cuttings path may be at least a portion of a shaker table. The capture of images by at least one of the hyperspectral camera and the optical camera may be synchronised with the frequency of movement of the shaker table.

In another aspect the invention provides a method of analysing drilling cuttings using output from a hyperspectral camera and at least one optical camera, comprising, generating hyperspectral imaging data comprising a line of hyperspectral imaging data derived from a line image taken by the hyperspectral camera positioned along a drilling fluid cuttings path at a first time, performing a mineralogy analysis on the data of the hyperspectral line, projecting the line of hyperspectral data onto an image from the optical camera output of a portion of the drilling fluid cuttings path that includes the hyperspectral imaging line position and corresponding to the first time, classify the mineralogy of the cuttings in the optical camera image along the projected line, and determine the morphology of the cuttings in the optical camera image.

The method of the second aspect may further comprise generating an image including the mineralogy and morphology information.

The invention also provides a system for analysing drilling cuttings using output from a hyperspectral camera and at least one optical camera, comprising a processing unit configured to, generate a hyperspectral imaging data set comprising a plurality of lines of hyperspectral imaging data derived from line images taken by a hyperspectral imaging device positioned along a drilling fluid cuttings path, obtain tracking information in respect of particles in the output of the at least one optical camera, correct the position of pixels associated with particles of interest in the plurality of lines of hyperspectral imaging data based on the obtained tracking information to generate corrected hyperspectral imaging data, and to analyse the corrected hyperspectral imaging data to characterise the cuttings.

The processing unit may be further configured to distinguish between background and particles of interest in image data from the optical camera of a portion of the drilling fluid cuttings path that includes the hyperspectral imaging line position, and to differentiate between particles of interest and background in the hyperspectral imaging data based on the distinguished background and particles of interest in the image date from the optical camera.

The processing unit may be further configured to track movement of particles in the optical camera output to obtain the tracking information and associate the particles of interest in the hyperspectral imaging data with the tracking information.

The processing unit may be configured to distinguish the particles of interest from the background using depth information.

The processing unit may be configured to differentiate between particles of interest and background in the hyperspectral imaging data by masking the distinguished particles of interest in the optical data, and applying the mask to the hyperspectral imaging data.

The tracking information may comprise speed of movement associated with pixels in the optical camera output.

The portion of the drilling fluid cuttings path is at least a portion of a shaker table.

The invention further comprises in an aspect a system for analysing drilling cuttings using output from a hyperspectral camera and at least one optical camera, comprising a processing unit configured to, generate hyperspectral imaging data comprising a line of hyperspectral imaging data derived from a line image taken by the hyperspectral camera positioned along a drilling fluid cuttings path at a first time, perform a mineralogy analysis on the data of the hyperspectral line, project the line of hyperspectral data onto an image from the optical camera output of a portion of the drilling fluid cuttings path that includes the hyperspectral imaging line position and corresponding to the first time, classify the mineralogy of the cuttings in the optical camera image along the projected line, and determine the morphology of the cuttings in the optical camera image.

In another aspect the invention provides a computer program comprising instructions which, when the program is executed by a computer, cause the computer to carry out any of the above methods according to aspects of the invention.

DRAWINGS

Embodiments of the invention will now be described in more detail, and by way of example only, with reference to the drawings, in which:

FIG. 2 is a schematic representation useful in a comparison for mapping between the 2D optical camera and a 1D hyperspectral inspection;

FIG. 3 is a schematic representation of the outputs of the HSI and optical cameras in respect of a single tracked cuttings particle;

DESCRIPTION

The invention combines hyperspectral imaging and one or more (high-speed) camera(s) for purposes of describing drilling cuttings and cavings, for example, while traversing a shale shaker or shaker table.

Figure 5:
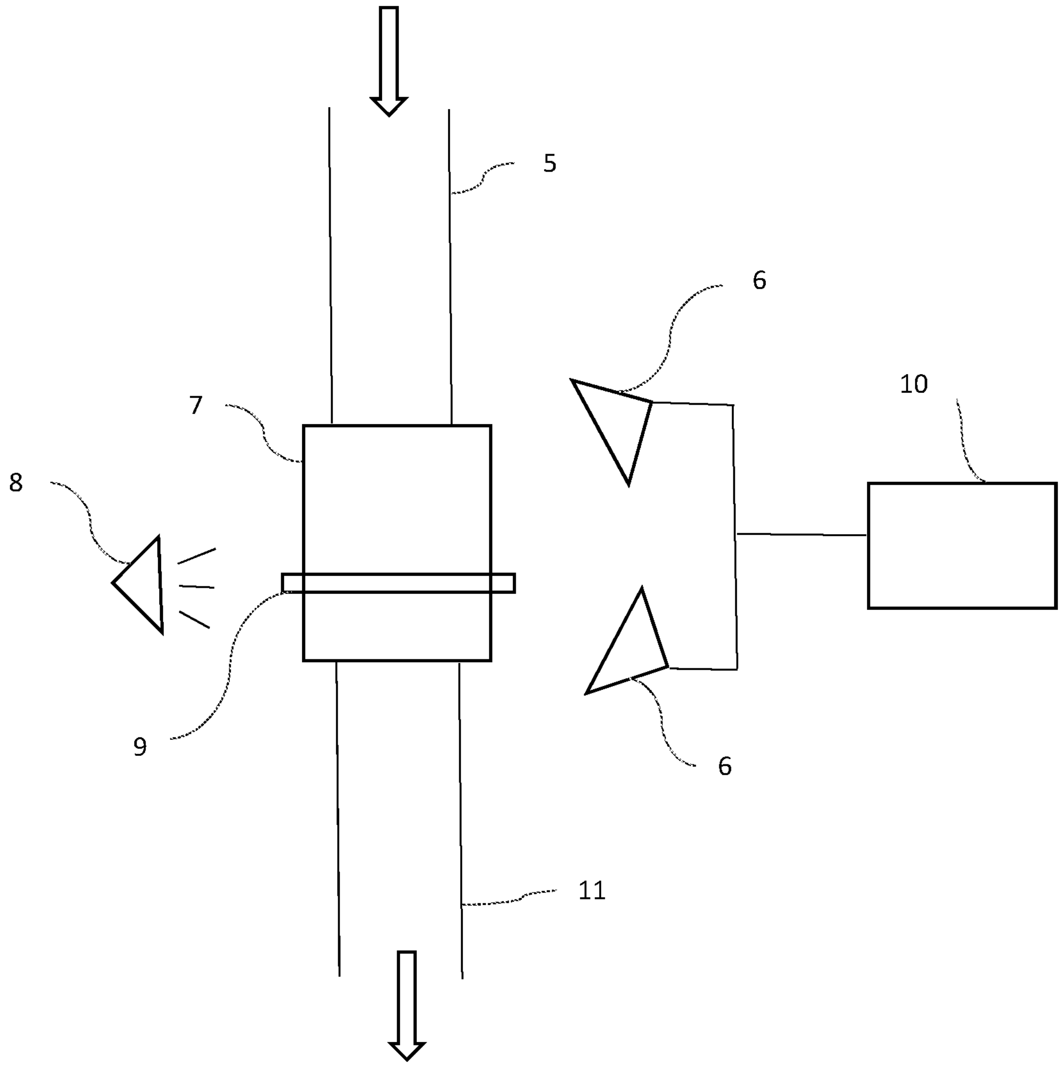
FIG. 5 shows schematically a system in accordance with an embodiment.

Apparatus according to an embodiment are shown schematically in FIG. 5. Drilling fluid returned from the downhole drilling process moves along return path 5 in the direction of shale shaker or shaker table 7. A single shaker table 7 is shown for convenience in FIG. 5. The return path continues after the shaker table 7 along path 11 to a disposal area for the cuttings. Typically the shale shaker includes a plurality of vertically arranged shaker tables with apertures of decreasing size down the stack so as to remove progressively finer particles. In this case path 11 may be in the form of a chute with the cuttings caught by each of the tables 7 being deposited down the chute 11. The upper shaker table 7 or scalping table removes the largest cuttings/cavings particles.

A short wave infrared 1D (line) hyperspectral camera 9 is positioned at suitable location above the shaker table 7 so as to be positioned for capturing a line of hyperspectral data as the drilling fluid and any cuttings pass beneath the hyperspectral camera 9. A 2D high speed optical camera system 6 is also located in order to capture a 2D image of the shaker table 7 and any drilling fluid and cuttings on the shaker table 7. In an embodiment the camera system 6 is a stereoscopic camera system shown schematically by the two camera sensors 6 in FIG. 5. The camera system 6 may include more or alternative sensors, including optical or video cameras, single or multi-stereo-cameras, night vision cameras, IR, LIDAR, RGB-D cameras, or other recording and/or distance-sensing equipment. The camera system 6 provides a 2D capture feed of at least a portion of the shaker table including the line covered by the hyperspectral camera 9. The data acquired by the camera system 6 (and the hyperspectral camera 9) is delivered to a processing unit 10 including the computer vision (CV) capability for analysing the 2D feed and extracting both the height information (for identifying cuttings particles and separating out the background) and the speed/motion information required for tracking the individual identified particles. The CV processing unit 10 may also include shape recognition software for determining the morphology of the identified particles. In an embodiment, Illumination is provided by lamp or lamps 8.

Computer Vision (CV) or Machine Vision software is well known, for example packages such HALCON™ from MVTec, are known, and allow development of applications for blob analysis, morphology, matching, measuring, and identification for example. Applying computer vision techniques to the output from the camera system 6 allows the signals captured using the two types of sensors (hyperspectral camera and computer vision (CV)) to be synchronised, making it possible to correlate the measurements from the sensors. Examples of applications/benefits of correlating measurements:

1. A 3D depth map from the CV system can be used to identify parts of the shaker covered by fluid only (no cuttings/cavings). This provides the HSI system with the ability to identify and (spectrally) define the fluid and/or shaker bed. In other words the depth information allows categorisation of the points in the HSI data that include cuttings from those that are just fluid or shaker table. The mineralogy identification algorithm can use this information to achieve better results since it is better able to distinguish between cuttings/cavings and the background. This procedure also allows the HSI system to provide more accurate (less contaminated) spectral data to the algorithm for mineralogical identification.

It should be noted that the larger particles will generally have less drilling fluid sticking to them. Identifying the larger particles, which have greater available surface area, also improves the confidence in the mineralogical identification.

2. Using the CV system to track particles as they move across the line scan makes it possible to correlate 1D HSI measurements of the same piece of rock. CV allows for tracking of cuttings (pixels representing at least a portion of an individual cutting entity) over the 2D area of interest.

Correlating as described above provides the ability to link cuttings and cavings in the returned drilling fluid to geological formations by linking to other drilling sensor or data analysis systems; in particular, the bit depth and the flow rate of the drilling fluid.

Determining the morphology of cuttings and the mineralogy allows labelling of the contents of the cuttings in the 2D image. In an embodiment the morphology and the mineralogy is determined from the HSI data, albeit the optical (e.g. 2D video) is used to enhance the morphology determination from the HSI data. Alternatively or additionally, morphology can be determine separately from the 2D output.

3. The 2D camera(s) allow a 2D (continuous) hyperspectral image to be constructed from a 1D HSI output, whilst correcting for different movement speeds along the shaker across the 1D scan line (using motion detector by CV system of identified pixels).

The hyperspectral camera of the embodiment is a 1D line Short Wave Infra-Red device. The 2D stereo camera feed is processed by the data processing unit or video processor to identify shapes of individual entities in the 2D frame. Since the signals are synchronised, the hyperspectral analysis can be mapped into 2D space (by time stamping the 1D hyperspectral image). The mineralogy from the hyperspectral system can then be mapped onto the (shape identified) cutting entities. In this manner, the morphology and mineralogy of an entity can be linked in accordance with the method of FIG. 1.

Figure 1:
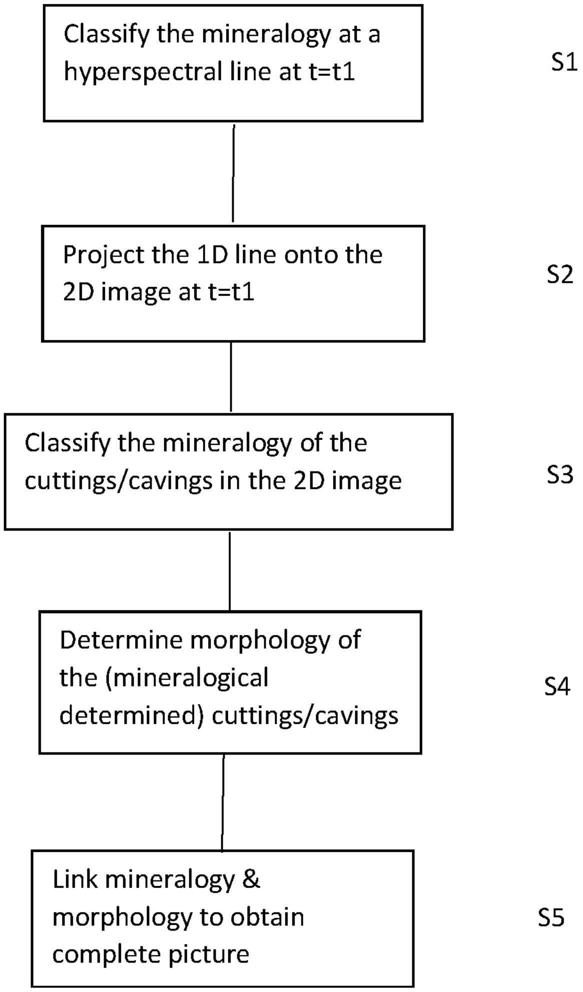
FIG. 1 is a flow diagram of a method in accordance with an embodiment.

The steps of the method of FIG. 1 are described in more detail with reference in addition to FIG. 2:

In step S1 of FIG. 1, a line of hyperspectral data taken by the HSI camera is classified by known techniques to determine the mineralogy present in the cuttings traversing the hyperspectral line at t=t1. At step S2 the 1D hyperspectral line is projected at time t=t1 onto a 2D image taken by optical (video) cameras of the shaker table 2 including the cuttings and cavings particles 1. The projection is required since the pixels in the 1D HSI image do not map one to one onto the 2D image taken by the camera system 6.

Whilst CV can be used for shape detection in the 2D image it is easier to perform boundary detection in the HSI data. Thus by clustering the HSI data and performing boundary detection, using the 2D depth map as additional data, the object boundaries can be more accurately determined.

In step S3 the cuttings and cavings particles 1 identified in the 2D image are classified with the mineralogy information determined in step S1. In step S4 the morphology of the cuttings and cavings particles 1 identified in the 2D image are determined using known CV techniques. Finally, in step S5 the mineralogy & morphology of each identified cuttings particle 1 are linked to obtain a complete picture, for example allowing a labelled representation of the cuttings particles on the shaker table to be displayed.

Whilst the above discussion and the flow chart in FIG. 1 imply an order to the steps, in fact the invention is not so limited and certain steps can be carried out in different orders so long as they do not rely on previous steps. In particular, the morphology of the cuttings/cavings can be determined before or in parallel with the previous steps.

A 2D image can be obtained from a succession of 1D lines of hyperspectral data as discussed below in relation to FIG. 3. In the case of a 1D hyperspectral imaging device, the shapes of the cuttings will be distorted owing to the different speed of movement of the different cuttings entities across the cuttings flow path across the 1D hyperspectral imaging location. Thus the cuttings particles 1 represented schematically in FIG. 2, are represented as having corresponding particles 1*a* with notional shapes that differ to the actual particles 1 as they appear on the shaker table 2.

As discussed above, particles (cuttings/cavings) recorded and presented in the HSI data appear deformed, for example due to the movement of the shaker table. CV provides the ability to identify the movement of each particle (in particular each pixel or group of pixels identified as associated with a single cuttings particle), thus also the speed of movement of each cuttings particle 1. Applying the speed information obtained from the CV data, to the particles identified in the HSI data, creates a new (2D 'continuous' HSI dataset constructed from a 1D line scanner), with corrected shapes.

Figure 4:
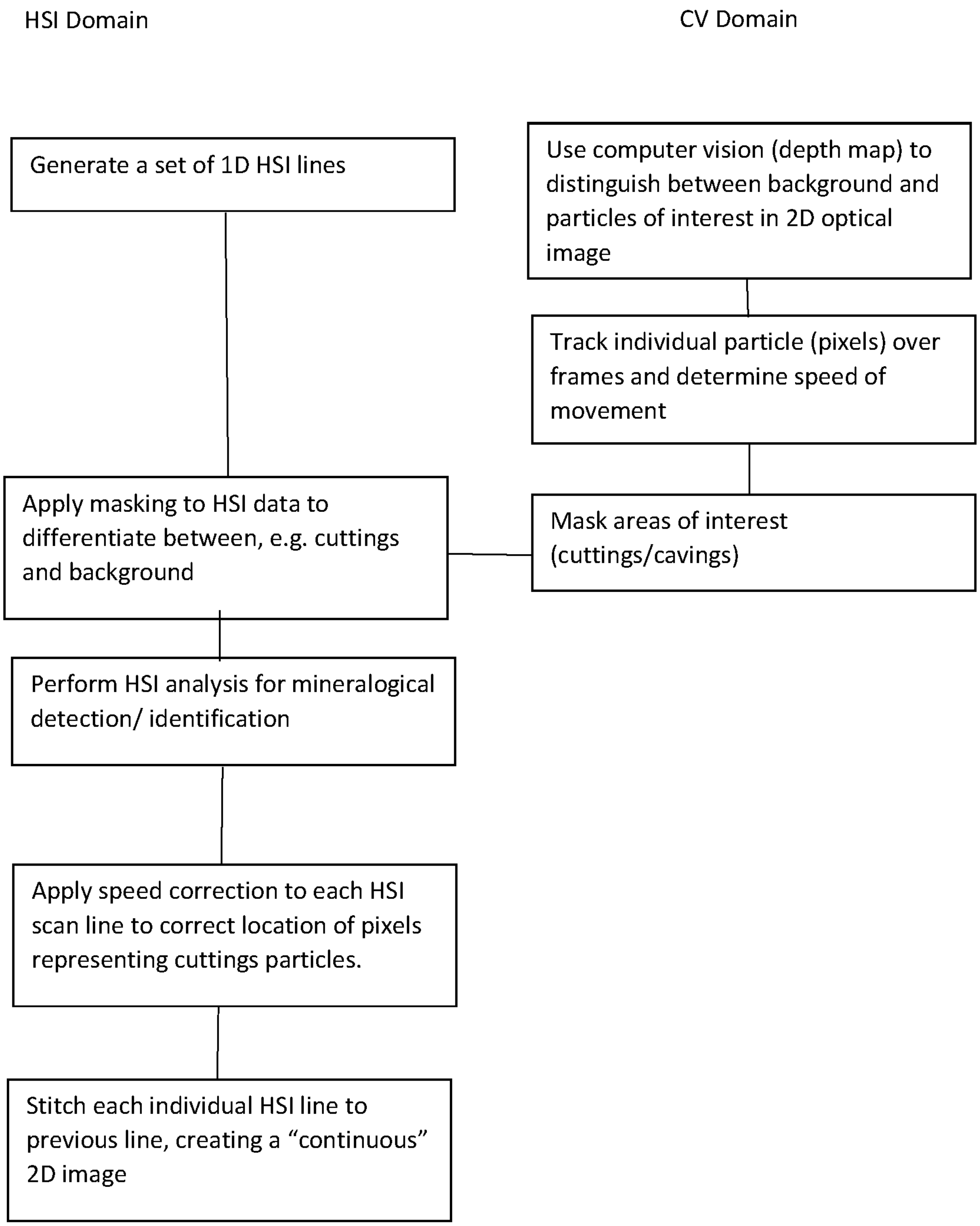
FIG. 4 is a flow diagram of a method in accordance with an embodiment.

Referring to FIGS. 3 and 4, FIG. 3 shows schematically images of the HSI domain on the left and the CV domain on the right, whereas FIG. 4 indicates the process steps of the HSI domain on the left and the process steps in the CV domain on the right.

The HSI scanner generates a set of successive HSI lines 3. The successive or series of HIS lines include position errors, which would result in deformed shapes of particles (particle pixels appear where they are located after a movement of the particle) (HSI domain).

Computer vision techniques, are used to distinguish between the background and particles of interest. In an embodiment a depth map is constructed using the optical camera output (CV domain). Additional sensors could be used instead of the camera system 6 to provide the depth information and the camera system could be used simply to provide an optical image and to allow object tracking. Conveniently, however, the camera system can also provide the depth information. Where an addition sensor system is used to provide the depth map, this must be synced and correlated with the optical camera output. Such systems are known from WO-A-2016077521. This document also discusses different ways of distinguishing between cuttings and background that may be used in the present invention, including, background subtraction/change detection either on the shaker bed or when falling off the shaker bed, identifying objects that move at approximately constant velocity as relating to cuttings, distinguishing the texture difference between cuttings and background, reflectivity and colour properties, persistence and/or tracking techniques. These and other known techniques may be used to distinguish between cuttings and background in the present invention.

Various techniques may be used to optimize the background removal process, for example, by synchronising the capture of the 2D and 1D image with the movement of the shaker, the moving shaker screen is in the same location on every image. For example, if the shaker vibrates at a particular frequency, the refresh rate of the cameras is set accordingly, for example, a multiple of the frequency.

If in addition, a picture is taken when the shaker screen is at stand-still (or pumps are off during drilling connection) then the background can be better defined by using the still shaker screen picture as a reference picture, in other words a base line for the algorithms can be based on the reference picture. It is then less likely that the shaker screen spectrum is mixed with rock or drilling fluid spectrum. Additionally or alternatively, images captured when only mud passes by (immediately after pumps on or not drilling), can be used for comparison to improve detection reliability.

The motion of the particles is tracked using standard CV techniques to track individual particles (pixels or groups of pixels) over frames and determine speed of movement of the particle (CV domain). In FIG. 3 the position of the particle in successive time stamped frames (t1 to t4) is shown schematically; the arrows indicate the movement of the particle between frames.

By distinguishing the background from the particles of cuttings and cavings and tracking the particles over time it is possible to mask areas of interest in the 2D image that is determined to relate to cuttings/cavings (CV domain).

By applying the mask to the 1D HIS data the data relating to cuttings/caving can be better distinguished from the background (fluid or shaker screen). From the HSI data the mineralogy detection/identification algorithm performed on each of the HSI lines 3 can be guided towards an enhanced mineralogy detection/identification result (HSI domain).

A full HSI analysis is performed on each of the spectral lines 3 to determine spectral identity (HSI domain).

Using the movement speed information determined in the CV domain and mapped on to the HSI data, speed correction can be applied to each line scan HSI data, to replace pixels to their new (corrected shape) location (HSI domain).

The plural spectral lines 3 with the corrected position data can be stitched together to provide a 'continuous' 2D HSI image that in a newly created representation 4 of spectrally labelled data with the location of each cutting/caving on a location determined by their first point of passing through the scan line with corrected 2D shapes.

By virtue of the method of the embodiment an improved virtual HSI cuttings/cavings representation can be provided with information relating to mineralogy and morphology of the cuttings/cavings.

Statistics can be extracted relating to shape, size distribution from the data and applied (labelled) in the representation. (HSI domain).

As a result of the above techniques, particularly, the combination of the data from the optical camera system and the HSI data, the cuttings and cavings in the drilling fluid can be more accurately described in terms of morphology and mineralogy. The mineralogy of each cutting particle can be better described, in particular, the distribution of minerals in the particles as a whole and in particular particles using the 2D representations of the individual particles from the HSI data.

In an embodiment, Illumination is provided by lamp or lamps 8. Data acquisition can be optimized by matching illumination and spectral characteristics with the specific hyperspectral camera 9. The lamp 8 may be a halogen or (thermal) infrared lamp for example. The lamp 8 may be adjusted by optimizing the bulb shape and/or reflector width and curvature so as to obtain maximum intensity along the HSI measuring line with a uniform distribution. Can also prevent overheating; if the light source causes an increase in temperature of the atmosphere above an ignition point then it can be dangerous.

The performance of data acquisition by the sensors 6, 9, may also be improved by selecting shaker screens with respect to sieve mesh and colour. In particular, so that the background can be distinguished more easily during the background removal process.

The mudflow speed may be modulated during measurements of data, for example intermittently paused to allow for a clearer picture.

Data acquisition may also be improved by adding means of spraying the shaker screen with a cleaning agent, like diesel or base oil, allowing for pictures of solids with less adhered fluids.

The invention claimed is:

1. A method of analyzing drilling cuttings using image data output from a hyperspectral imaging device and at least one optical camera, comprising:

generating a hyperspectral imaging data set comprising a plurality of lines of 1D hyperspectral imaging data derived from line images taken by the hyperspectral imaging device positioned along a drilling fluid cuttings path;

obtaining tracking information with respect to particles of interest from the output of the at least one optical camera;

correcting the position of pixels associated with particles of interest in the plurality of lines of 1D hyperspectral imaging data based on the obtained tracking information to generate corrected hyperspectral imaging data that is stitched together to provide a 2D HSI image with corrected shapes; and analyzing the corrected hyperspectral imaging data to characterize the cuttings, wherein correcting is applied to each individual 1D lines in an HSI domain prior to stitching the 2D image with corrected shapes.

2. The method as claimed in claim 1, further comprising, distinguishing between background and particles of interest in the optical camera output of a portion of the drilling fluid cuttings path that includes the hyperspectral imaging line position, and differentiating between particles of interest and background in the hyperspectral imaging data based on the step of distinguishing.

3. The method as claimed in claim 1, further comprising tracking movement of particles in the optical camera output to obtain the tracking information and associating the particles of interest with the tracking information.

4. The method as claimed in claim 1, further comprising obtaining depth information, wherein the particles of interest are distinguished from the background using the depth information.

5. The method of claim 1, wherein differentiating between particles of interest and background in the hyperspectral imaging data comprises masking particles of interest in the optical data based on the step of distinguishing, and applying the mask to the hyperspectral imaging data to differentiate between particles of interest and background in the hyperspectral imaging data.

6. The method of claim 1, wherein associating the particles of interest with tracking information comprises determining the speed of movement associated with pixels in the optical camera output.

7. The method of claim 1, wherein the portion of the drilling fluid cuttings path is at least a portion of a shaker table.

8. The method of claim 7 wherein the capture of images by at least one of the hyperspectral camera and the optical camera are synchronized with the frequency of movement of the shaker table.

9. The method of claim 1, wherein the tracking information comprises speed of movement associated with pixels in the optical camera output.

10. A computer program embodied on a non-transitory computer readable medium and comprising instructions which, when the program is executed by a computer, cause the computer to carry out the method of claim 1.

11. A system for analyzing drilling cuttings using output from a hyperspectral camera and at least one optical camera, comprising a processing unit configured to:

generate a hyperspectral imaging data set comprising a plurality of lines of 1D hyperspectral imaging data derived from line images taken by a hyperspectral imaging device positioned along a drilling fluid cuttings path;

obtain tracking information with respect to particles in the output of the at least one optical camera;

correct the position of pixels associated with particles of interest in the plurality of lines of 1D hyperspectral imaging data based on the obtained tracking information to generate corrected hyperspectral imaging data that is stitched together to provide a 2D HSI image with corrected shapes; and analyze the corrected hyperspectral imaging data to characterize the cuttings, wherein correcting is applied to each individual 1D lines in an HSI domain prior to stitching the 2D image with corrected shapes.

12. The system of claim 11, wherein the processing unit is further configured to distinguish between background and particles of interest in image data from the optical camera of a portion of the drilling fluid cuttings path that includes the hyperspectral imaging line position, and to differentiate between particles of interest and background in the hyperspectral imaging data based on the distinguished background and particles of interest in the image date from the optical camera.

13. The system of claim 11, wherein the processing unit is further configured to track movement of particles in the optical camera output to obtain the tracking information and associate the particles of interest in the hyperspectral imaging data with the tracking information.

14. The system of claim 11, wherein the processing unit is configured to distinguish the particles of interest from the background using depth information.

15. The system of claim 11, wherein the processing unit is configured to differentiate between particles of interest and background in the hyperspectral imaging data by masking the distinguished particles of interest in the optical data, and applying the mask to the hyperspectral imaging data.

16. The system of claim 11, wherein the tracking information comprises speed of movement associated with pixels in the optical camera output.

17. The system of claim 11, wherein the portion of the drilling fluid cuttings path is at least a portion of a shaker table.

* * * * *